United States Patent [19]

Kraus

[11] Patent Number: 5,599,998
[45] Date of Patent: Feb. 4, 1997

[54] METHOD FOR THE SYNTHESIS OF ADAMANTANE AMINES

[75] Inventor: George A. Kraus, Ames, Iowa

[73] Assignee: Iowa State University Research Foundation, Inc., Ames, Iowa

[21] Appl. No.: 327,615

[22] Filed: Oct. 24, 1994

[51] Int. Cl.$^6$ ................................................. C07C 209/66
[52] U.S. Cl. ........................ 564/455; 564/458; 570/187
[58] Field of Search .................................. 564/445, 458; 570/187

[56] References Cited

U.S. PATENT DOCUMENTS

| 3,388,164 | 6/1968 | Curran et al. ............................ 260/563 |
| 3,391,142 | 7/1968 | Mills et al. ............................. 260/268 |
| 3,705,916 | 12/1972 | Bower .................................. 260/429.3 |

OTHER PUBLICATIONS

E. Erdik et al., "Electrophilic Amination of Carbanions," *Chem. Rev.*, 89, 1947–1980 (1989).
B. H. Han et al., "Organic Sonochemistry, Ultrasound–Promoted Coupling of Organic Halides in the Presence of Lithium Wire," *Tet. Lett.*, 22, 2757–2758 (1981).
G. Molle et al., "Synthese de Molecules Encombrees; Recherche des Conditions Optimales de Condesation des Composes Organolithiens cage sur Differents Substrats Organiques," *Tetrahedron*, 40, 5113–5119 (1984).
March, Advanced Organic Chemistry, John Wiley & Sons: New York, pp. 449–451 (1992).
H. B. Abrahamson et al., "Spectroscopy and Photochemistry of the Tetranorbornyl Complexes of Titanium and Chromium," *Organometallics*, 3, 1379 (1984).
*Aldrichimica Acta*, 18, 82 (1985).
P. Beak et al., "A Modification of the Sheverdina–Kocheshkov Amination": The Use of Methoxyamine–Methyllithium as a Convenient Synthetic Equivalent for $NH_2^+$," *J. Org. Chem.*, 47, 2822–2823 (1982).
R. Brown et al., "A Convenient Method of Preparation of Certain Primary Amines," *J. of the Chem. Soc.*, Part II, 781 (1946).
E. K. Byrne et al., "Synthesis, Characterization, and Electron–Transfer Reactivity of Norbornyl Complexes of Cobalt in Unusually High Oxidation States", *J. Am. Chem. Soc.*, 111, 3887–3896 (1989).
E. Ciganek, "Tertiary Carbinamines by Addition of Organocerium Reagents to Nitriles and Ketimines," *J. Org. Chem.*, 57, 4521 (1992).
M. J. Eis et al., "$BF_3$–Etherate Promoted Alkylation of Azirdines with Organocopper Reagents: A New Synthesis of Amines," *Tetrahedron Letters*, 26, 1153 (1985).
E. Erdik et al., "Electrophilic Amination of Carbanions", *J. Am. Chem. Soc.*, 89, 1947–1980 (1989).
K. Gerzon et al., "The Adamantyl Group in Medicinal Agents. I. Hypoglycemic N–arylsulfonyl–N'–adamantylureas," *J. Med. Chem.*, 6, 760 (1963).
H. Gilman et al., *Organic Reactions*, VIII, 259 (1953).
W. D. Graham et al., "Diamond Lattice Hydrocarbons, Spiro[adamantane–2,2'–adamantane]", *Tetra. Letters*, 12, 1179–1180 (1972).

C. E. Hoffman, "Amantadine HCl and Related Compounds," *Selective Inhibitors of Viral Functions*, 200 (1972).
J. C. Kauer et al., "Aliphatic Cyanates," *J. of Am. Chem. Soc.*, 86, 4732 (1964).
J. Kirschbaum, "Amantadine," *Analytical Profiles of Drug Substances*, 12, 1 (1983).
B. J. Kokko et al., "The Electrophilic Amination of Organolithiums with Methyllithium Complexes of N–Substituted Methoxyamines", *Tetra. Letters*, 24, 561–564 (1983).
P. Kovacic et al., "Amination of Adamantanes and Their Precursors with Trichloramine–Aluminum Chloride," *J. of Am. Chem. Soc.*, 91, 6457 (1969).
G. A. Kraus et al., "Bridgehead Intermediates in Organic Synthesis. A Reproducible Synthesis of Adamantane–Containing Compounds", *J. Org. Chem.*, 59, 922–923 (1994).
P. S. Manchand et al., "Synthesis and Antiviral Activity of Metabolites of Rimantadine," *A. Che. Soc.*, 33, 1992 (1990).
G. Molle et al., "Organometallic Compounds with Cage Structures: 1–Adamantyl Lithium", *Synthetic Comm.*, 8(1), 39–43 (1978).
G. Molle et al., "Cage Structure Organometallic Compounds: 1–Diamantyl, 1–Twistyl, 1–Triptycyl and 2–adamantyl Lithium Compounds, Synthesis and Reactivity", *Tetra Letters*, 34, 3177–3180 (1978).
G. Molle et al., "Formation of Cage–Structure Organomagnesium Compounds. Influence of the Degree of Adsorption of the Transient Species at the Metal Surface", *J. Org. Chem.*, 47, 4120–4128 (1982).
G. Molle et al., "High–Yield Direct Synthesis of a New Class of Tertiary Organolithium Derivatives of Polycyclic Hydrocarbons", *J. Org. Chem.*, 48, 2975–2981 (1983).
T. Morimoto et al., "N,N–Bis(trimethylsilyl)methoxymethylamine as a Convenient Synthetic Equivalent for $^+CH_2NH_2$ : Primary aminomethylation of Organometallic Compounds," *J. Chem. Soc., Chem. Commun.*, 12, 794 (1984).
S. Rozen et al., "Direct Synthesis of Fluoro Bicyclic Compounds with Fluorine," *J. Org. Chem.*, 53, 2803 (1988).
K. B. Wiberg et al., "Bicyclo[1.1.1]pentane Derivatives," *J. Org. Chem.*, 35, 369 (1970).
J. H. Wieringa et al., "1–Lithioadamantane", *Synthetic Comm.*, 2(4), 191–195 (1972).
J. H. Wieringa et al., "2–Lithioadamantane," *Synthetic Comm.*, 1(1), 7 (1971).
T.–C. Wu et al., "Organocalcium Chemistry: Preparation and Reactions of Highly Reactive Calcium", *J. Org. Chem.*, 55, 5045–5051 (1990).
D. M. Zlydnikov et al., "Study of Rimantadine in the USSR: A Review of the Literature," *Revs. of Infectious Diseases*, 3, 408 (1981).

*Primary Examiner*—Brian M. Burn
*Attorney, Agent, or Firm*—Schwegman, Lundberg, Woessner & Kluth, P.A.

[57] ABSTRACT

The present invention provides a method to prepare aminated bridgehead polycyclic hydrocarbons by reacting bridgehead halo polycyclic hydrocarbons with lithium metal under conditions of sonication and aminating the resultant lithio compounds.

11 Claims, No Drawings

METHOD FOR THE SYNTHESIS OF ADAMANTANE AMINES

BACKGROUND OF THE INVENTION

The government has certain rights in the invention.

Compounds containing the adamantane subunit have long been of interest to chemists due to the rigid structure and well-defined substitution chemistry of adamantane. The discovery of the potent antiviral activity of amantidine (1-aminoadamantane) and rimantadine (α-methyl-1-adamantylmethylamine) (3) has stimulated interest in the synthesis of adamantine-containing compounds. The significant neuroprotective properties of the NMDA antagonist memantine (1-amino-3,5-dimethyladamantane) (2) have also prompted interest in adamantane synthesis.

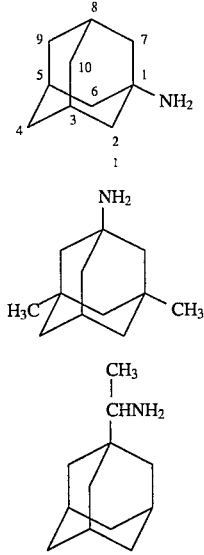

Numerous syntheses of 1-aminoadamantane ($AdNH_2$) have been reported, many of which proceed via degradation of more complex functional groups at the bridgehead position. For example, Curran et al. (U.S. Pat. No. 3,388,164) disclose a method comprising reacting adamantane-1-carboxylic acid with a sodium azide in a mixture of trifluoroacetic acid and trifluoroacetic anhydride to form 1-trifluomacetamido-adamantane, and hydrolyzing the 1-trifluoroacetamidoadamantane to obtain 1-adamantaneamine. See also, J. Mills et al. (U.S. Pat. No. 3,391,142).

Although the carbocation chemistry of the adamantane system has been extensively studied, the chemistry of adamantyl bridgehead anions has been addressed only in a few isolated publications. No study of the scope and limitations of the preparation of adamantyl bridgehead anions has been reported. Moreover, the literature of this bridgehead anion is complicated by problems related to reproducibility of experimental protocols. G. Molle et al., *J, Org. Chem.*, 47, 4120 (1982), reported that stirring a two-phase mixture of 1-bromoadamantane (AdBr) and magnesium actually decreased the yield of Grignard reagent AdMgBr, as compared with allowing the two-phase mixture to stand without stirring. 1-Lithioadamantane (AdLi) has been prepared by the reaction of 1-chloroadamantane (AdCl) in pentane with an excess of 2% sodium lithium alloy. During the synthesis, the alloy was scoured by stiffing the reaction mixture with crushed glass. The resultant AdLi (4) was treated with nonenolizable ketones to provide hindered alcohols in modest yields. See G. Molle et al., *Tetrahedron Lett.*, 34, 3177 (1976); G. Molle et al., *J. Org. Chem.*, 48, 2975 (1983). Recently, Rieke and co-workers, *J. Org. Chem.*, 55, 5045 (1990), prepared an activated calcium reagent which reacted with adamantyl bromide to generate an organocalcium reagent which, upon reaction with cyclohexanone, afforded an 80% yield of alcohol 5; as shown in Scheme I, below:

Scheme I

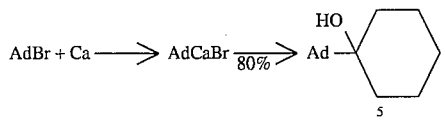

However, the successful conversion of AdLi to yield 1-aminoadamantanes has not been reported.

Therefore, a need exists for an improved synthesis of 1-aminoadamantanes.

SUMMARY OF THE INVENTION

The present invention provides a method for derivatizing 1-halo adamantanes comprising reacting a compound of formula (I):

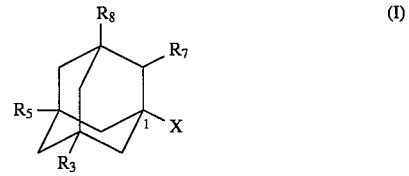

wherein each $R_3$, $R_5$, $R_7$, and $R_8$ is H, F or $CH_3$ and X is Br, Cl or I, with lithium metal in an organic solvent, such as an ether, under sonication to yield a compound of formula (I) where X is Li.

The invention further comprises reacting the compound of formula I wherein X is Li with an aminating agent in situ in the reaction mixture under conditions of sonication to yield a compound of formula I wherein X is $N(R)_2$, $CH_2CH_2N(R)_2$ or $C(R^1)_2N(R)_2$ wherein each R and $R^1$ is H, $(C_1-C_8)$alkyl, $(C_6-C_{10})$ aryl or $(C_7-C_{18})$aralkyl, preferably R' is $CH_3$ and R is H. A preferred compound of formula I is the formula:

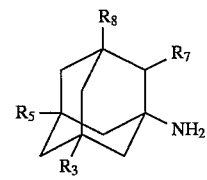

wherein $R_3$, $R_5$ and $R_7$ are defined above and $R_8$ is H; or where $R_3$, $R_5$ and $R_8$ are as defined above, and $R_7$ is H. The present invention is particularly advantageous in that it proceeds without the use of heterologous particulate scouring agents and can be carried out without application of external heat.

DETAILED DESCRIPTION OF THE INVENTION

The present methodology is also expected to be generally applicable for the bridgehead lithiation of halogenated polycycles of the general formula II:

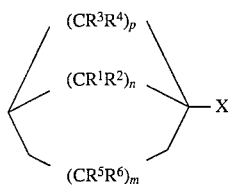

wherein X is Cl, Br or I; p=1 or 2, n=0–2, m=0–2 and $R^1$, $R^2$, $R^3$, $R^4$, $R^5$ and $R^6$ are individually H, or $(C_1-C_4)$lower alkyl, preferably $CH_3$. Preferably alkyl is $(C_1-G_2)$alkyl and, as used herein, the term "alkyl" includes branched or straight chain alkyls. Also, when p=n=m=2, each (CRR) group can be 1,2-phenylene.

Thus, representative halogenated polycyclic hydrocarbons useful as starting materials in the present method include adamantane derivatives such as 1-bromo-3-methyladamantane, 1-bromo-, and 1-chloro-3,5,7-trimethyladamantane, and 1-bromo-3,5-dimethyladamantane. Other "cage" hydrocarbon derivatives such as 1-chlorodiamantane, 3-chloro-homoadamantane, 3-halo-7-methylnoradamantane (3-chloro-7-methylnoradmnantane), 1-bromotriptycene, 1-chloro-twistane, and the like can also be lithiated and aminated by the present method. These compounds are commercially available or can be prepared as disclosed in G. Molle et al., *J. Org. Chem.*, 48, 2975 (1983), the disclosure of which is incorporated by reference herein. Bridgehead fluoroadamantanes can be prepared using elemental fluorine as disclosed by S. Rozen et al., *J. Org. Chem.*, 53, 2803 (1988).

Useful solvents include hydrocarbons and/or organic ethers, such as di$(C_1-C_4)$alkylethers, tetrahydrofuran, glycol ethers and mixtures thereof. The sonication of the reaction mixture can be accomplished externally, using commercially available equipment, such as ultrasound baths. The lithiation and amination reactions are preferably conducted under ambient conditions or at lower temperatures, i.e., at about –10° C. to 30° C., most preferably at about –5° C.–+5° C., using external cooling.

Useful aminating reagents include a hydroxylamine-O-sulfonate, methoxylamine-$CH_3Li$, $NH_2Cl$ or di-tert-butyl-azodicarboxylate. The use of methoxyamine-methyl lithium complex to convert organolithium compounds into primary amines is disclosed, e.g., by P. Beak et al., *J. Org. Chem.*, 47, 2822 (1982) and by N. J. Shevercline et al., in *J. Gen. Chem. USSR*, 8, 1825 (1938). N-alkyl-methoxyamines can also be used to form secondary amines from the lithioadamantanes as disclosed by R. J. Kokko et al., *Tet. Lett.*, 24, 561 (1983).

Preferably, the aminating reagent is added portionwise following initiation of sonication of a reaction mixture comprising lithium metal and a solution of the compound of formula I or II. Following addition of the aminating reagent, the sonication can be continued for an appropriate period of time to maximize the yield of the product.

Compound I or II, X=Li, can also be reacted with an activated aziridine to form a polycyclic compound substituted at the bridgehead position with a 2-aminoethyl group or can also be reacted with an imine to form a polycyclic compound substituted at the bridgehead position with a 2-aminomethyl group. These reactions are summarized in Scheme II below, for 1-lithioadamantane.

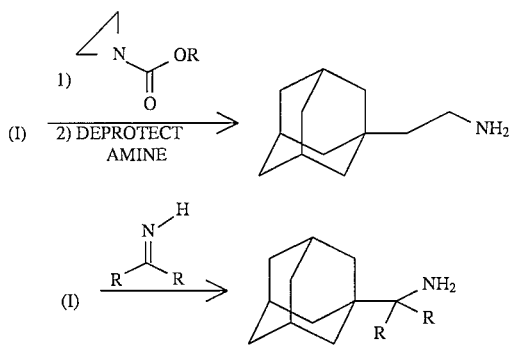

Each R can individually be $(C_1-C_8)$lower alkyl, $(C_6-C_{10})$aryl, $(C_7-C_{18})$aralkyl and the like. Mono- or disubstituted-bridgehead amino compounds, wherein R is $(C_1-C_8)$alkyl, aryl, aralkyl or mixtures thereof with H, can be prepared by conventional methods for the conversion of primary amino groups to secondary or tertiary amino groups. For example, see I. T. Harrison et al., *Compendium of Organic Synthetic Methods*, Wiley-Interscience, N.Y. (1971) at pages 240–246. Preferred aryl groups include $(C_6-C_{10})$ aryl groups substituted with 1–3 $(C_1-C_8)$alkyl, halo, $(C_1-C_4)$alkoxy and the like, including phenyl, tolyl, xylyl, anisyl, and the like. Preferred aralkyls include those in which said aryl groups are joined to the amino group by a $(C_1-C_8)$ straight-chain or branched alkyl group, in which 1–2 carbons are optionally replaced by —O—, S, or —N(R)—, e.g., aralkyl is preferably $C_7-C_{18}$, wherein the aryl portion is optionally substituted as above.

Pharmaceutically acceptable acid salts of the present amines can be prepared as described in U.S. Pat. No. 4,383,114.

The compounds of formula I include the known antiviral agents amantadine and rimantadine, and the muscle relaxant memantine, and would be expected to exhibit similar spectra of bioactivities. For example, see D. M. Zlydnikov et al., *Rev. Infect. Dis.*, 3, 408 (1981); P.-A. Fischer et al., *Arzneimittel—Forsch.*, 32, 1236–76 (1982); and J. Kirschbaum, *Anal. Profiles of Drug Substances*, 12, 1–36 (1983).

The invention will be further described by reference to the following detailed examples.

General Procedure: Li wire (6 mm in length, 3 mm diameter, 9.6 mmol) was cut into small pieces under $N_2$ and was added to a dry, $N_2$-flushed flask. $Et_2O$ (8 mL) was then added, followed by a solution of anhydrous 1-bromoadamantane (410 mg, 1.9 mmol) in 2 mL of $Et_2O$. The flask was placed in an ultrasound bath containing water and crushed ice and sonication was started. Five equiv of the aminating agent was added dropwise via a syringe. The mixture was further sonicated. The flask was then removed from the bath and 15 mL of $H_2O$ were added. The product was separated from the organic phase by sgc with hexanes/ethyl acetate as eluant.

The compounds listed in Table I, below, were made using this procedure.

TABLE I

| Ex. | Aminoadamantane | Aminating Agent | Yield |
|---|---|---|---|
| 1. | 1-Aminoadamantane | $NH_2Cl$ | 54 |
| 2. | 1-Amino-3,5-dimethyl adamantane | $NH_2Cl$ | 48 |

TABLE I-continued

| Ex. | Aminoadamantane | Aminating Agent | Yield |
|---|---|---|---|
| 3. | 2-Aminonorbornane | NH$_2$Cl | 39 |
| 4. | Tritylamine | NH$_2$Cl | 67 |
| 5. | 1-Aminotriptycene | NH$_2$Cl | 41 |
| 6. | 1-Aminotriptycene | [(t-BuO$_2$C)N=]$_2$ | 48 |

All publications and patents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for derivatizing 1-halo-adamantanes comprising reacting a compound of formula (I):

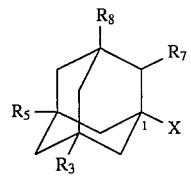

(I)

wherein each of wherein each of R$_3$, R$_5$, R$_7$ and R$_8$ is H, F or CH$_3$ and X is Br, Cl or I, with lithium metal in an organic solvent, under sonication, to yield a compound of formula (I), wherein X is Li.

2. The method of claim 1 further comprising reacting the compound of formula (I), wherein X is Li with an aminating agent to yield a compound of formula (I), wherein X is selected from a group consisting of N(R)$_2$, —CH$_2$CH$_2$N(R)$_2$ or —C(R')$_2$N(R)$_2$, wherein each R and R' is individually H, (C$_1$–C$_8$)alkyl, (C$_6$–C$_{10}$)aryl, or (C$_7$–C$_{18}$)aralkyl.

3. The method of claim 2 wherein each R' is (C$_1$–C$_4$)alkyl and each R is H or CH$_3$.

4. The method of claim 2 wherein one R' is CH$_3$ and one R' is H.

5. The method of claim 2 wherein X is NH$_2$.

6. The method of claims 1 or 2 where R$_8$ is H.

7. The method of claim 5 wherein R$_3$, R$_5$, R$_7$, and R$_8$ are H.

8. The method of claim 5 wherein R$_3$ and R$_5$ are CH$_3$ and R$_7$ and R$_8$ are H.

9. The method of claim 1 wherein the organic solvent is an ether.

10. The method of claims 1 or 2 wherein the reaction is carried out at about −10° C. to 25° C.

11. The method of claim 1 wherein X is Br.

\* \* \* \* \*